US009497971B2

(12) United States Patent
Baker et al.

(10) Patent No.: US 9,497,971 B2
(45) Date of Patent: Nov. 22, 2016

(54) NON-VOLATILE ORGANIC COMPOUND PESTICIDE FORMULATIONS

(71) Applicant: Bayer CropScience LP, Research Triangle Park, NC (US)

(72) Inventors: Robert Britt Baker, Cary, NC (US); Kurt P. Vandock, Creedmoor, NC (US); Gary Gore, Four Oaks, NC (US); Byron Reid, Raleigh, NC (US)

(73) Assignee: Bayer CropScience LP, Research Triangle Park, NC (US)

( * ) Notice: Subject to any disclaimer, the term of this patent is extended or adjusted under 35 U.S.C. 154(b) by 0 days.

(21) Appl. No.: 14/629,824

(22) Filed: Feb. 24, 2015

(65) Prior Publication Data

US 2016/0242418 A1 Aug. 25, 2016

(51) Int. Cl.
*A01N 53/00* (2006.01)
*A01N 25/02* (2006.01)
*A01N 25/14* (2006.01)

(52) U.S. Cl.
CPC ............... *A01N 53/00* (2013.01); *A01N 25/02* (2013.01); *A01N 25/14* (2013.01)

(58) Field of Classification Search
CPC ....... A01N 53/00; A01N 25/02; A01N 25/14
See application file for complete search history.

(56) References Cited

U.S. PATENT DOCUMENTS

| | | | |
|---|---|---|---|
| 5,466,458 A | 11/1995 | Martin et al. | |
| 5,527,823 A | 6/1996 | Martin et al. | |
| 5,827,522 A | 10/1998 | Nowak | |
| 5,968,990 A | 10/1999 | Jon et al. | |
| 6,200,961 B1 | 3/2001 | Kostka et al. | |
| 6,551,964 B1 | 4/2003 | Bardsley et al. | |
| 6,693,131 B2 | 2/2004 | Noeding et al. | |
| 8,119,150 B2 | 2/2012 | Tamarkin et al. | |
| 2008/0096763 A1 | 4/2008 | Dawson et al. | |
| 2008/0254988 A1 | 10/2008 | Wang et al. | |
| 2009/0163582 A1* | 6/2009 | Wang | A01N 25/06 514/464 |
| 2009/0275601 A1 | 11/2009 | Taylor et al. | |
| 2009/0297871 A1 | 12/2009 | Crimp et al. | |
| 2010/0093715 A1 | 4/2010 | Voeste et al. | |
| 2010/0216641 A1 | 8/2010 | Wang et al. | |
| 2010/0322990 A1 | 12/2010 | Burke et al. | |
| 2012/0053151 A1 | 3/2012 | Pedersen | |
| 2013/0183261 A1 | 7/2013 | Harada et al. | |
| 2013/0217579 A1 | 8/2013 | Wacker et al. | |
| 2013/0345110 A1 | 12/2013 | Volont et al. | |
| 2014/0013654 A1 | 1/2014 | Burke | |
| 2014/0031424 A1 | 1/2014 | Humphrey et al. | |

FOREIGN PATENT DOCUMENTS

| | | |
|---|---|---|
| WO | 2013044449 A1 | 4/2013 |
| WO | 2014049347 A1 | 4/2014 |

OTHER PUBLICATIONS

International Search Report mailed Mar. 16, 2016 in counterpart U.S. Application No. PCT/US2016/019420.

* cited by examiner

*Primary Examiner* — Kara R McMillian
(74) *Attorney, Agent, or Firm* — McBee Moore Woodward Vanik IP, LLC.

(57) ABSTRACT

Water-based formulations (EW) are provided containing no VOC's or alternatively are low in VOC's for wide area space spray to control mosquitoes, flies, and other public health pests. Application via ULV, these formulations have been observed to provide significantly superior control of pests when compared to competitive adulticides. The present formulations provide exceptional preservation of both droplet density in the spray cloud and droplet size as measured by volume mean diameter (VmD). The present formulations provide superior bio-efficacy as measured by both mortality and knockdown of target organisms. The present formulations provide superior biological control, droplet density, and droplet size when applied at concentrations 20-80× less than competitive formulations.

16 Claims, No Drawings

NON-VOLATILE ORGANIC COMPOUND PESTICIDE FORMULATIONS

BACKGROUND

1. Field

The present disclosure relates to spray formulations, especially pesticidal formulations of the sort which may be diluted with water to form a sprayable preparation, for example, a pressure pack ("aerosol") preparation or a spray, particularly an ultra-low volume (ULV) spray for domestic, horticultural, agricultural, environmental, or industrial use. In particular, the present disclosure relates to pesticidal formulations devoid of Volatile Organic Compounds.

2. Description of Related Art

Water-based sprays are advantageous because they cost less than oil-based sprays and are often less toxic to mammals. However, particularly when the ambient temperature is high, the water in the spray droplets evaporates and the droplets become smaller and drift more readily from the area being sprayed. The size of the droplets is frequently specially chosen to suit the application, for example to maximize droplet adherence to flying insects or adherence to plant foliage, to increase bio-availability, or to control the size of the area being sprayed and the delivery rate per square meter; such care is pointless if the spray droplets change size, possibly unpredictably, following spraying.

Water-in-oil emulsions are typically used in water-based sprays due to the low solubility of most pesticides in water. Volatile Organic Compound (VOC) regulations, however, have limited the compounds that are available to formulate water-in-oil emulsions suitable for pesticide applications. Thus, there is a significant need to develop further pesticidal formulations with low VOC content.

Chemical pesticides are of critical importance in maintaining control of diseases spread by mosquitoes and other insects, particularly in developing countries. However, there is growing resistance to the most commonly used chemical pesticides, including pyrethroids, DDT, carbamates, and organophosphates. Thus, it is critical to develop pesticidal formulations that kill more efficiently to reduce formation of resistance in these disease-carrying pests.

The solution to this technical problem is provided by the embodiments characterized in the claims.

BRIEF SUMMARY OF THE INVENTION

The present application relates to spray formulations, especially pesticidal formulations of the sort which may be diluted with water to form a sprayable preparation, for example, a pressure pack ("aerosol") preparation or a spray, particularly an ultra-low volume (ULV) spray for domestic, horticultural, agricultural, environmental, or industrial use. In particular, the present disclosure relates to pesticidal formulations devoid of Volatile Organic Compounds (VOC).

In particular, the present application provides spray formulations comprising at least one active ingredient and at least one solvent. In addition, the spray formulation optionally comprises a humectant, an emulsifier, an anti-foam agent and/or a preservative, together with other ingredients such as perfumes, dyes, solids (especially to form wettable powders) and thickeners.

The active ingredient may be an insecticide, acaricide, herbicide, fungicide, plant growth regulator, insect behavior modifier, biological control agent (e.g. viruses, bacteria, and eggs of parasites), dye, perfume, bactericide, lubricant, medicament, paint, polish, lacquer (including hair lacquer), textile treatment (including sizes), or other compound to be sprayed in a water-based formulation. Sprays in accordance with the invention are particularly suitable for spraying buildings, residential or commercial areas, and insect breeding grounds (such as swamps and other tracts of water) with insecticide and for spraying crops with herbicides, insecticides, fungicides, and plant growth regulators.

The sprays may be delivered by pumping through a nozzle, especially a sonic nozzle, by pumping over an ultrasonic nebulizer, or via a spinning disc. The droplets may be electro-statically charged, if desired.

Suitable pesticides include pyrethroids (such as permethrin, deltamethrin, cypermethrin (including alphamethrin, the allethrins, fenvalerate, transfluthrin, and cyfluthrin), organophosphates (such as ethion, chlorfenvinphos, chlorpyrifos (methyl) or coumaphos), carbamates, organochlorines (such as DDT, dieldrin, dicofol, chlorpropylate, or tetradifon), lipid amides, bicyclooctanes, dithianes, pyrethrins, pyrethrum, chloronicotinics, pyrazoles, butenolides, terpenoids, fiproles, tetramic acid derivatives (ketoenols), tetranilliproles, or biological insecticides. Suitable herbicides include glyphosate. Suitable larvicides (IGRs, biologics) include methoprene, *Bacillus thuringiensis israelensis* (Bti), *Bacillus sphaericus* (Bs), organophosphates (such as temephos), and pyriproxyfen. Suitable solvents are Volatile Organic Compounds (VOC)-exempt or contain no VOCs. Suitable non-VOC solvents include, but are not limited to, acetate esters, methyl esters, acetyl-tributyl citrate, isoparaffinic fluids, paraffinic fluids, vegetable oils such as canola oil, cotton seed oil, soybean oil and the like, and mixtures thereof. Suitable VOC-exempt solvents include, but are not limited to, monoethylene, diethylene, triethylene, tetraethylene glycols, and polyethylene glycols such as PEG 300 and above. Preferably, the solvent is acetyl-tributyl citrate.

DETAILED DESCRIPTION

Before the subject disclosure is further described, it is to be understood that the disclosure is not limited to the particular embodiments of the disclosure described below, as variations of the particular embodiments may be made and still fall within the scope of the appended claims. It is also to be understood that the terminology employed is for the purpose of describing particular embodiments, and is not intended to be limiting. Instead, the scope of the present disclosure will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this disclosure belongs.

The term "spray formulation" is defined as a formulation, especially pesticidal formulations, of the sort which may be diluted with water to form a sprayable preparation, for example, a pressure pack ("aerosol") preparation or a spray, particularly an ultra-low volume (ULV) spray for domestic, horticultural, agricultural, environmental or industrial use.

The terms "VOC-exempt" and "Volatile organic compound-exempt" are used interchangeably throughout this specification and the appended claims and are defined according to the definition under U.S. Environmental Protection Agency (EPA) regulations under 40 C.F.R. §59.203 (f). These EPA regulations define a chemical as "VOC-exempt" if it has vapor pressure of less than 0.1 millimeters of mercury (at 20° C.). If the vapor pressure is unknown, a chemical is defined as "VOC-exempt" if it a) consists of more than 12 carbon atoms; or b) has a melting point higher than 20° C. and does not sublime (i.e., does not change directly from a solid into a gas without melting).

ULV sprays are generally used in space spray insecticides to treat or fog areas to kill adult mosquitoes. An insecticide is diluted and atomized by a ULV fogging machine. The insecticide would then be released from the ground or from the air. Air currents would carry the droplets downwind of the application equipment. The droplets would collide with the insects, coating the insect with a lethal dose of the active ingredient.

Water dilutable insecticides include formulations such as the FFAST™ (an acronym for Film Forming Aqueous Spray Technology) insecticide formulations described in U.S. Pat. Nos. 5,466,458, 5,527,823, and 6,302,161 allow for the use of water as a diluent. These patents are hereby incorporated by reference.

It is generally less expensive and more desirable to have the option of using a water-based product. However, at ambient temperatures, conventional water-based sprays tend to evaporate quickly and fail to deliver the insecticide to the target insects or pests efficiently. To overcome this problem in the past, dispersing insecticides in water required the creation of large droplets. However, these large droplets did not drift efficiently and did not reach the target at all.

A formulation, such as the FFAST™ formulation, using long chain alcohol molecules to form a protective film around each droplet of insecticide as it leaves the nozzle of the sprayer, allows for the formation of droplets that do not evaporate too quickly and that efficiently deliver the insecticide to the target insect. The incorporation of long chain alcohols into the formulation provides a means of coating the individual droplets of insecticides when mixed with water so as to control the rate of evaporation. This film retards the evaporation of the droplets and they maintain the desired optimum size.

The subject disclosure features, in one aspect, spray formulations comprising at least one active ingredient and at least one solvent. In addition, the spray formulation optionally comprises a synergist, a humectant, an emulsifier, an anti-foam agent and/or a preservative. In a preferred embodiment, the spray formulations are Volatile Organic Compounds (VOC)-exempt or alternatively, contain no VOCs. The U.S. Environmental Protection Agency (EPA) identifies a VOC as an organic compound that participates in atmospheric photochemical reactions, but makes exceptions for compounds that have negligible photochemical reactivity. VOCs are emitted as gases from certain solids or liquids. They include a variety of chemicals, some of which may have short- and long-term adverse health effects. Conventional emulsified pesticide formulations generally contain 50-90% by weight VOCs. Current regulations from the California Department of Pesticide Regulation and from the U.S. Environmental Protection Agency (EPA) recommend that pesticides are formulated to contain 20% by weight VOC, or less.

VOC content may be measured by any method known in the art. Several states, including California, evaluate methods and maintain lists of approved tests available for determining VOC content. One established method of determining the VOC content is a gas chromatographic analysis in accordance with DIN EN ISO 11890-2.

Thus, in a preferred embodiment, the spray formulations are low in VOC. In particular, the spray formulations contain ≤16% VOC by weight. In a more preferred embodiment, the spray formulations contain ≤10% VOC by weight, ≤5% VOC by weight, or ≤2.5% VOC by weight.

In a more preferred embodiment, the spray formulations are devoid or essentially devoid of VOC by weight. In particular, the spray formulations contain ≤1% VOC by weight. Optionally, the spray formulations contain ≤0.5% VOC by weight, ≤0.25% VOC by weight, ≤0.1% VOC by weight, or ≤0.05% VOC by weight.

Active ingredients of the invention include pesticides. In particular, the pesticide may be a pyrethroid, an organophosphate, a carbamate, an organochlorine, a lipid amide, a bicyclooctane, a dithiane, a pyrethrin, a pyrethrum, a chloronicotinic, a pyrazole, butenolide, a terpenoid, a fiprole, a tetramic acid derivative (ketoenol), a tetranilliprole, or a biological insecticide.

In a preferred embodiment of the invention, the active ingredient is one or more pyrethroid. Examples of pyrethroid insecticides include those of the formula (I)

$$\text{(I)}$$

and n is 0 or 1, $R^1$ is halo CR3 or CHF2O, R2 is hydrogen or halo, and Z and Z1 are each independently selected from halo, CF3 and methyl, X is hydrogen or halo, and X is H, CN or C≡CH or or Examples of pyrethroids include, but are not limited to, 3-phenobenzyl-(1RS)-cis,trans-3-(2,2-dichlorovinyl-2,2-dimethyl-cyclopropane-1-carboxylate (permethrin), (RS)-α-cyano-3-phenoxybenzyl-(1RS)-cis,trans-3-(2,2-dichlorovinyl)-2,2-dimethylcyclopropane-1-carboxylate (cypermethrin) and its individual isomers such as the (1RS) cis isomer (alphamethrin), (S)-α-cyano-3-phenoxybenzyl-(1R)-cis-3-(2,2-dibromovinyl)-2,2-dimethyl cyclopropane-1-carboxylate (deltamethrin), or a reaction mixture comprising two enantiomeric pairs in approximately ratio 2:3 (S)-α-cyano-3-phenoxybenzyl-(1R)-cis-3-(2,2-dichlorovinyl)-2,2-dimethylcyclopropanecarboxylate and (R)-α-cyano-3-phenoxybenzyl-(1S)-cis-3-(2,2-dichlorovinyl)-2,2-dimethylcyclopropanecarboxylate with (S)-α=cyano-3-phenoxybenzyl-(1R)-trans-3-(2,2-dichlorovinyl)-2,2-dimethylcyclopropanecarboxylate and (R)-α-cyano-3-phenoxybenzyl-(1S)-trans-3-(2,2-dichlorovinyl)-2,2-dimethylcyclopropanecarboxylate (beta-cypermethrin), (RS)-α-cyano-3-phenoxybenzyl-(Z)-(1RS)-cis-3-(2-chloro-3,3,3-trifluoropropenyl)-2,2-dimethylcyclopropanecarboxylate (cyhalothrin) and a mixture of its (S)(Z)-(1R)-cis and (R)(Z)-(1S)-cis isomers; (RS)-α-cyano-3-phenoxybenzyl (RS)-2-(4-chlorophenyl)-3-methylbutyrate (fenvalerate) and the single (S), (S) isomer (esfenvalerate) (RS)-α-cyano-3-phenoxybenzyl (S)-2-(4-difluoromethoxyphenyl)-3-methyl butyrate (flucythinate), (RS)-α-cyano-3-phenoxybenzyl N(2-chloro-α,α,α-trifluoro-p-tolyl)-D-valinate (fluvalinate), (RS)-α-cyano-4-fluoro-3-phenoxybenzyl(1RS)-cis-trans-3-(2,2-dichlorovinyl)-2,2-dimethylcyclopropanecarboxylate (cyfluthrin), (RS)-α-cyano-4-fluoro-3-phenoxybenzyl (1RS)-cis-trans-3-(2-chloro-2(4-chlorophenyl)vinyl)-2,2-dimethylcyclopropanecarboxylate (flumethrin), 2-methylbiphenyl-3-yl-methyl(Z)-(1RS,3RS)-3-(2-chloro-3,3,3-trifluoroprop-1-enyl)2,2-dimethylcyclopropanecarboxylate (Bifenthrin); the allethrins, for example (1RS)-3-allyl-2-methyl-4-oxocylopent-2-enyl)cyclopropanecarboxylate (bioallethrin), (1S)-allyl-2-methyl-4-oxocyclopent-2-enyl (1R,3R)-2,2-dimethyl-3-(2-methylprop-1-enyl)cyclopropanecarboxylate (S-bioallethrin), and mixtures of allethrin isomers (esbiothrin); the resmethrins, for example 5-benzyl-3-furylmethyl(1RS-3RS; 1RS, 3SR)-2,2-dimethyl-3-(2-methyl-prop-1-enyl)cyclopropanecarboxylate (resmethrin), 5-benzyl-3-furylmethyl (1R,3R)-2,2-dimethyl-3-(2-methyl-prop-1-enyl)cyclopropanecarboxylate (bioresmethrin), and 2,3,5,6-tetrafluorobenzyl (1R,3S)-3-(2,2-dichlorovinyl)-2,2-dimethylcyclopropanecarboxylate (transfluthrin), 2,3,5,6-tetrafluoro-4-(methoxymethyl)benzyl (EZ)-(1RS,3RS;1RS,3SR)-2,2-dimethyl-3-prop-1-enylcyclopropanecarboxylate (metofluthrin), and pyrethroids with a polyfluorobenzyl group.

Examples of organophosphate insecticides include, but are not limited to, 0,0-dimethyl-0-3,5,6-trichloro-2-pyridylphosphorothioate (Chloropyri-fos-methyl).

Examples of formamidine insecticides include, but are not limited to, N-methyl bis(2,4-xylylaminomethyl)amine (Amitraz). Examples of thiazole anthelmintics include, but are not limited to, 2,3,5,6-tetrahydro-6-phenylimidazo[2,1-b]thiazole (levamisole).

Examples of fungicides include, but are not limited to, tributyl tin oxide.

Examples of pyrazole insecticides include, but are not limited to, 3-bromo-1-(3-chloro-2-pyridinyl)-N-[4-cyano-2-methyl-6-[(methylamino)carbonyl]phenyl]-1H-pyrazole-5-carboxamide (cyantraniliprole).

Examples of fiprole insecticides include, but are not limited to, 5-amino-1-[2,6-dichloro-4-(trifluoromethyl)phenyl]-4-[(trifluoromethyl)sulfinyl]-1H-pyrazole-3-carbonitrile (fipronil) and 5-amino-1-[2,6-dichloro-4-trifluoromethyl)phenyl]-4-[(ethyl)-sulfinyl]-1H-pyrazole-3-carbonitrile (ethiprole).

Examples of tetramic acid derivatives include, but are not limited to, cis-3-(2,5-dimethylphenyl)-8-methoxy-2-oxo-1-azaspiro[4.5]dec-3-en-4-yl-ethyl carbonate (suspirotetramat) and 2-oxo-3-(2,4,6-trimethylphenyl)-1-oxaspiro[4,4]non-3-en-4-yl 3,3-dimethylbutanoate (spiromesifen).

Examples of butenolides include, but are not limited to, 4-[[(6-chloropyridin-3-yl)methyl](2,2-difluoroethyl)amino]furan-2(5H)-one (flupyradifurone [Sivanto®]).

The formulations of the invention may contain one or more synergists. A synergist is defined as a chemical that does not possess inherent pesticidal activity, but instead promotes or enhances the effectiveness of pesticides when combined. Examples of synergists include, but are not limited to, bucarpolate, dietholate, jiajizengxiaolin, octachlorodipropyl ether, piperonyl butoxide (PBO), piperonyl cyclonene, piprotal, propyl isome, sesame, sesamolin, sulfoxide, tribufos, and zengxiaoan.

The active ingredient(s) of the formulation should be soluble in the solvent. In one embodiment, the solvent is tri-butyl citrate. In a more preferred embodiment, the solvent is acetyl tributyl citrate (CITROFLEX® A4).

The emulsifier may be any suitable compound or mixture of compounds. Cationic emulsifiers can be used, but they tend to irritate the users' eyes. Anionic emulsifiers such as calcium dodecyl benzene sulphate (CDBS) or sodium di-isopropyl naphthalene sulphonate (SDNS) can also be used, but these are not as effective at stabilizing the emulsion. Preferably, the emulsifier is a non-ionic compound, or mixture of non-ionic compounds, having an HLB (hydrophilic/lipophilic balance of 8-18. Suitable compounds include polyoxyethylene stearyl ethers (PSE), polyoxyethylene monolaurates (PEM), polyoxyethylene mono-oleates (PMO), sorbitan mono-oleate (SMO), nonylphenol ethoxylate (NPE), polyethylene glycol (PEG) and blends of oleyl ethoxylate (10 mole) and PEG20 glyceryl oleate (OE/PGO).

In a preferred embodiment, the emulsifier is polyoxyethylene (10) oleyl ether, polyoxyethylene (20) stearyl ether, ethoxylated castor oil, or polyoxyethylene (20) sorbitan monooleate.

The anti-foam agent may be any suitable compound or mixture of compounds. Exemplary compounds include SIL-COLAPSE® 426R or SILCOLAPSE® 432 (i.e. polyorganosiloxane aqueous emulsion).

Constituents may be present in 100% oil phase. Alternatively, the oil phase may comprise up to 45% of the formula and the water phase may comprise up to 55% of the formula wherein all other components are dissolved/dispersed in both phases. In a preferred embodiment, the oil phase is approximately 38% of the formulation and the water phase is approximately 62% of the formulation wherein all other constituents are dissolved/dispersed in both the oil and water phase.

The formulations of the instant invention may be used, for example, to control or prevent pest infestation. Thus, the invention comprises a method for controlling and/or preventing pest infestation comprising administering the formulation to an area susceptible to pest infestation.

Examples of pests that may be controlled by the formulations of the invention include, but are not limited to, mosquitoes, flies, and other public health pests, including, but not limited to cockroaches, bedbugs, sand flies, and reduviidae. Additional examples of pests that may be controlled by the formulations of the invention include, but are not limited to, stored product pests and rural hygiene pests.

Examples of areas that are susceptible to pest infestation which may be treated with the formulations of the invention include, but are not limited to, complex canopies. A complex canopy is defined as an area that is difficult to penetrate with typical pesticide formulations. Examples of complex canopies include, but are not limited to, dense vegetation and/or complex environments.

In an additional embodiment, the formulations of the instant invention can be used as a fumigant. Areas which may be treated according to this embodiment include areas of habitation. Examples of areas of habitation include, but are not limited to, indoor livestock facilities, outdoor livestock facilities, product storage areas, housing, office spaces, retail spaces, warehouses, and shipping containers.

The formulations of the instant invention are preferably wide-area space sprays applied via ULV to control mosquitoes, flies, and other public health pests. Preferably, the formulations of the instant invention can be applied via truck, backpack blower, drone, or helicopter.

Formulations of the invention have been observed to provide significantly superior control of pests when compared to competitive adulticides when applied via ULV. Specifically, it was discovered that formulations of the invention provide exceptional preservation of both droplet density in the spray cloud and droplet size as measured by volume mean diameter (VmD). The improved physical properties of the instant formulations are directly related to their superior bio-efficacy, measured by both mortality and knockdown of target organisms (i.e. mosquitoes). The present formulations provide superior biological control, droplet density, and droplet size when the active ingredient is applied at a concentration that is 20-80× less than competitive formulations.

In a preferred embodiment, application of the formulations of the invention via ULV provides a total average droplet density of $\geq 0.3$ drops/mm$^2$/fl oz of applied product. In a more preferred embodiment, application of the formulations of the invention via ULV provides a total average droplet density of $\geq 0.4$ drop s/mm$^2$/fl oz of applied product. In a more preferred embodiment, application of the formulations of the invention via ULV provides a total average droplet density of $\geq 0.5$ drop s/mm$^2$/fl oz of applied product. In a more preferred embodiment, application of the formulations of the invention via ULV provides a total average droplet density of $\geq 0.7$ drops/mm$^2$/fl oz of applied product. In a more preferred embodiment, application of the formulations of the invention via ULV provides a total average droplet density of $\geq 1$ drop/mm$^2$/fl oz of applied product.

In an additional preferred embodiment, application of the formulations of the invention via ULV provides a total droplet density of $\geq 750$ drops/mm$^2$/lb active ingredient/acre. In a more preferred embodiment, application of the formulations of the invention via ULV provides a total droplet density of $\geq 1000$ drops/mm$^2$/lb active ingredient/acre. In a more preferred embodiment, application of the formulations of the invention via ULV provides a total droplet density of $\geq 1500$ drops/mm$^2$/lb active ingredient/acre. In a more preferred embodiment, application of the formulations of the invention via ULV provides a total droplet density of $\geq 2000$ drops/mm$^2$/lb active ingredient/acre. In a more preferred embodiment, application of the formulations of the invention via ULV provides a total droplet density of $\geq 3000$ drops/mm$^2$/lb active ingredient/acre. In a more preferred embodiment, application of the formulations of the invention via ULV provides a total droplet density of $\geq 5000$ drops/mm$^2$/lb active ingredient/acre.

In an additional preferred embodiment, application of the formulations of the invention via ULV provides a variance in droplet density over a distance of 300 feet of 0.1 or less. In a more preferred embodiment, application of the formulations of the invention via ULV provides a variance in droplet density over a distance of 300 feet of 0.01 or less. In a more preferred embodiment, application of the formulations of the invention via ULV provides a variance in droplet density over a distance of 300 feet of 0.001 or less. In a more preferred embodiment, application of the formulations of the invention via ULV provides a variance in droplet density over a distance of 300 feet of 0.0005 or less.

A formulation suitable for spraying or for dilution with water to form a sprayable preparation, the formulation comprising at least one active ingredient and at least one solvent, wherein the formulation comprises 16% VOC by weight or less, wherein the reduction in VOC concentration results in improved efficacy and/or lower environmental impact.

A formulation suitable for spraying or for dilution with water to form a sprayable preparation, the formulation comprising at least one active ingredient and at least one solvent, wherein the formulation is VOC-exempt, wherein the reduction in VOC concentration results in improved efficacy and/or lower environmental impact.

The formulation, wherein said formulation contains no VOC.

The formulation, wherein said at least one active ingredient is one or more pyrethrum, pyrethroid, pyrethrin, chloronicotinic, carbamate, organophosphate, pyrazole, butenolide, terpenoid, fiprole, tetramic acid derivative, tetranilliprole and/or biological insecticides.

The formulation, wherein said at least one active ingredient is in either an aqueous phase, solubilized phase, or oil dispersion.

The formulation, wherein said at least one active ingredient is a pyrethroid.

The formulation, wherein said at least one active ingredient is deltamethrin.

The formulation, wherein said solvent is acetyl tributyl citrate.

The formulation, further comprising one or more emulsifier, anti-foam agent, and/or preservative.

The formulation, wherein the formulation is an ultra-low volume concentrate.

The formulation, wherein the formulation is a wettable powder.

The formulation, further comprising at least one synergist selected from the group consisting of: bucarpolate, dietholate, jiajizengxiaolin, octachlorodipropyl ether, piperonyl butoxide (PBO), piperonyl cyclonene, piprotal, propyl isome, sesame, sesamolin, sulfoxide, tribufos, and zengxiaoan.

The formulation, wherein the formulation provides at least one of the following: exceptional preservation of droplet density in the spray cloud, and/or droplet size as measured by volume mean diameter (VmD).

A method for controlling or preventing pest infestation, the method comprising administering the formulation to an area susceptible to pest infestation.

The method, wherein the formulation is an ultra-low volume concentrate.

The method, wherein the pest is a mosquito.

The method, wherein the area susceptible to pest infestation is a complex canopy.

The method, wherein said complex canopy is selected from the group consisting of: dense vegetation, and complex environment.

The method, wherein administration of the formulation provides a total average droplet density of ≥0.3 drops/mm$^2$/fl oz of applied product.

The method, wherein administration of the formulation provides a total droplet density of ≥750 drops/mm$^2$/lb active ingredient/acre.

The method, wherein administration of the formulation provides a variance in droplet density over a distance of 300 feet of 0.1 or less.

Use of the formulation to control or prevent pest infestation.

The use, wherein the formulation is applied to an area susceptible to pest infestation.

The use, wherein the formulation is an ultra-low volume concentrate.

The use, wherein the pest is a mosquito.

The use, wherein the area susceptible to pest infestation is a complex canopy.

The use, wherein said complex canopy is selected from the group consisting of: dense vegetation, and complex environment.

The use, wherein administration of the formulation provides a total average droplet density of ≥0.3 drops/mm$^2$/fl oz of applied product.

The use, wherein administration of the formulation provides a variance in droplet density over a distance of 300 feet of 0.1 or less.

The following Examples describe exemplary embodiments of the invention. These Examples should not be interpreted to encompass the entire breadth of the invention.

EXAMPLES

The efficacy of a non-VOC insecticide formulation of the invention was compared with several commercially available pyrethroid adulticides using a ground ULV sprayer against field populations of *Culex tarsalis* and *Aedes melanimon*. The non-VOC insecticide formulation of the invention (Formulation 1) was applied at low and average rates (i.e., 2 fl oz/min and 4 fl oz/min). In contrast, the commercially available insecticides were applied at the maximum label rates from three distances (100 ft, 200 ft, and 300 ft).

Droplet density was assessed during application. At 24 hours following treatment, mortality was assessed. The findings are presented below.

Table 1 summarizes the data comparing Formulation 1 to several commercially available pyrethroid insecticides. These data demonstrate the superior efficacy of Formulation 1 at very low rates compared to other commercial insecticides.

TABLE 1

| Product | Active Ingredient(s) | Formulation Type | Rate (lb ai/acre) | Fl. oz/min @ 10 MPH | Distance (ft) | 24 hr mortality (%) | Avg 24 hr mortality (%) | Droplet Density (drops/mm$^2$) |
|---|---|---|---|---|---|---|---|---|
| Formulation 1 | Deltamethrin | Water-based | 0.00045 | 2.02 | 100 | 99 | 95.00 | 1.08 |
|  |  |  |  |  | 200 | 96.9 |  | 1.05 |
|  |  |  |  |  | 300 | 89.1 |  | 1.02 |
| Formulation 1 | Deltamethrin | Water-based | 0.00089 | 4.04 | 100 | 99.2 | 99.73 | 4.74 |
|  |  |  |  |  | 200 | 100 |  | 4.75 |
|  |  |  |  |  | 300 | 100 |  | 4.71 |
| DUET ™ | Sumithrin/Prallethrin | Water-based | 0.0108 | 7.40 | 100 | 96.9 | 91.83 | 1.49 |
|  |  |  |  |  | 200 | 92.7 |  | 0.91 |
|  |  |  |  |  | 300 | 85.9 |  | 0.61 |
| ANVIL ® | Sumithrin | Oil-based | 0.0036 | 19.70 | 100 | 99 | 90.00 | 5.55 |
|  |  |  |  |  | 200 | 91.6 |  | 1.16 |
|  |  |  |  |  | 300 | 79.4 |  | 1.27 |
| Zenivex ® | Etofenprox | Oil-based | 0.007 | 18.00 | 100 | 83.4 | 80.40 | 3.77 |
|  |  |  |  |  | 200 | 83.2 |  | 2.96 |
|  |  |  |  |  | 300 | 74.6 |  | 2.35 |
| Scourge ® | Resmethrin | Oil-based | 0.007 | 18.00 | 100 | 97.5 | 97.03 | 5.61 |
|  |  |  |  |  | 200 | 96.2 |  | 3.02 |
|  |  |  |  |  | 300 | 97.4 |  | 6.54 |

The use, wherein administration of the formulation provides a total droplet density of ≥750 drops/mm$^2$/lb active ingredient/acre.

This increase in efficacy is further demonstrated by comparison of average droplet density of the applied insecticide per fluid ounce of applied insecticide as shown in Table 2.

TABLE 2

| Product | Active Ingredient(s) | Formulation Type | fl oz/min @ 10 MPH | Avg Droplet Density (drops/mm$^2$) | Avg Droplet Density (drops/mm$^2$)/fl oz Product |
|---|---|---|---|---|---|
| Formulation 1 | Deltamethrin | Water-based | 2.02 | 1.05 | 0.52 |
| Formulation 1 | Deltamethrin | Water-based | 4.04 | 4.73 | 1.17 |
| DUET ™ | Sumithrin/Prallethrin | Water-based | 7.40 | 1.00 | 0.14 |
| ANVIL ® | Sumithrin | Oil-based | 19.70 | 2.66 | 0.14 |

TABLE 2-continued

| Product | Active Ingredient(s) | Formulation Type | fl oz/min @ 10 MPH | Avg Droplet Density (drops/mm$^2$) | Avg Droplet Density (drops/mm$^2$)/fl oz Product |
|---|---|---|---|---|---|
| ZENIVEX ® | Etofenprox | Oil-based | 18.00 | 3.03 | 0.17 |
| SCOURGE ® | Resmethrin | Oil-based | 18.00 | 5.06 | 0.28 |

Illustrated another way, formulations of the invention also demonstrate a significant advantage in total droplet density as measured by droplet density per pound of active ingredient per acre (droplet density/lb ai/acre) as shown in Table 3.

TABLE 3

| Product | Active Ingredient(s) | Formulation Type | Rate (lb ai/acre) | Avg Droplet Density (drops/mm$^2$) | Droplet Density/lb ai/acre |
|---|---|---|---|---|---|
| Formulation 1 | Deltamethrin | Water-based | 0.00045 | 1.05 | 2333.33 |
| Formulation 1 | Deltamethrin | Water-based | 0.00089 | 4.73 | 5310.86 |
| DUET ™ | Sumithrin/Prallethrin | Water-based | 0.0108 | 1.00 | 92.90 |
| ANVIL ® | Sumithrin | Oil-based | 0.0036 | 2.66 | 738.89 |
| ZENIVEX ® | Etofenprox | Oil-based | 0.007 | 3.03 | 432.38 |
| SCOURGE ® | Resmethrin | Oil-based | 0.007 | 5.06 | 722.38 |

Additionally, there is superior lack in variability in droplet density over distance during application of Formulation 1 compared to other commercially available pyrethroid insecticides as shown in Table 4.

TABLE 4

| Product | Active Ingredient(s) | Formulation Type | Rate (lb ai/acre) | Average Droplet Density (drops/mm$^2$) | Variance in Droplet Density over 300' |
|---|---|---|---|---|---|
| Formulation 1 | Deltamethrin | Water-based | 0.00045 | 1.05 | 0.0009 |
| Formulation 1 | Deltamethrin | Water-based | 0.00089 | 4.73 | 0.0004 |
| DUET ™ | Sumithrin/Prallethrin | Water-based | 0.0108 | 1.00 | 0.2001 |
| ANVIL ® | Sumithrin | Oil-based | 0.0036 | 2.66 | 6.2671 |
| ZENIVEX ® | Etofenprox | Oil-based | 0.007 | 3.03 | 0.5074 |
| SCOURGE ® | Resmethrin | Oil-based | 0.007 | 5.06 | 3.3272 |

As illustrated in the above tables, the non-VOC formulation of the invention performed better than both the water-based and oil-based pyrethroid commercial formulations in both mortality and in droplet density. This is a remarkable finding since the non-VOC formulation of the invention was applied at low or mid-range rates in comparison to the commercial formulations applied at the maximum rate. This indicates that in addition to the environmental benefit of being devoid in VOCs, the formulations of the invention are also able to provide superior control with far less pesticide (on a total volume and lb ai/acre basis) to be released into the environment.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior invention.

It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A formulation diluted with water to form a sprayable diluted formulation, the formulation comprising deltamethrin and acetyl tributyl citrate, wherein the diluted formulation contains no VOCs.

2. The formulation of claim 1, wherein said formulation further comprises one or more pyrethrum, pyrethroid, pyrethrin, chloronicotinic, carbamate, organophosphate, pyrazole, butenolide, fiprole, tetramic acid derivative, tetraniliprole and/or biological insecticides.

3. The formulation of claim 1, wherein said deltamethrin is in either an aqueous phase, solubilized phase, or oil dispersion.

4. The formulation of claim 1, further comprising one or more emulsifier, anti-foam agent, and/or preservative.

5. The formulation of claim 1, wherein the formulation is an ultra-low volume concentrate.

6. The formulation of claim 1, wherein the formulation is a wettable powder.

7. The formulation of claim 1, further comprising at least one synergist selected from the group consisting of: bucarpolate, dietholate, jiajizengxiaolin, octachlorodipropyl ether, piperonyl butoxide (PBO), piperonyl cyclonene, piprotal, propyl isome, sesame, sesamolin, sulfoxide, tribufos, and zengxiaoan.

8. The formulation of claim 1, wherein the formulation provides at least one of the following: exceptional preservation of droplet density in the spray cloud, and/or droplet size as measured by volume mean diameter (VmD).

9. A method for controlling or preventing pest infestation, the method comprising administering the formulation of claim 1 to an area susceptible to pest infestation.

10. The method of claim 9, wherein the formulation is an ultra-low volume concentrate.

11. The method of claim 9, wherein the pest is a mosquito.

12. The method of claim 9, wherein the area susceptible to pest infestation is a complex canopy.

13. The method of claim 12, wherein said complex canopy is selected from the group consisting of: dense vegetation, and complex environment.

14. The method of claim 10, wherein administration of the formulation of claim 1 provides a total average droplet density of ≥0.3 drops/mm$^2$/fl oz of applied product.

15. The method of claim 10, wherein administration of the formulation of claim 1 provides a total droplet density of ≥750 drops/mm$^2$/lb active ingredient/acre.

16. The method of claim 10, wherein administration of the formulation of claim 1 provides a variance in droplet density over a distance of 300 feet of 0.1 or less.

* * * * *